United States Patent [19]

Schultz et al.

[11] 3,996,302
[45] Dec. 7, 1976

[54] PROCESS FOR PURIFYING 1,1,1-TRIFLUORO-2-CHLORO-2-BROMOETHANE

[75] Inventors: Neithart Schultz, Eichsel; Hans-Joachim Vahlensieck, Wehr, both of Germany

[73] Assignee: Dynamit Nobel Aktiengesellschaft, Troisdorf, Germany

[22] Filed: Mar. 19, 1975

[21] Appl. No.: 559,991

Related U.S. Application Data

[63] Continuation of Ser. No. 224,628, Feb. 8, 1972, abandoned.

[30] Foreign Application Priority Data

Apr. 28, 1971 Germany .......................... 2120756

[52] U.S. Cl. ............................................. 260/653
[51] Int. Cl.² .................. C07C 17/38; C07C 19/08
[58] Field of Search .................................... 260/653

[56] References Cited

UNITED STATES PATENTS

| 3,004,075 | 10/1961 | Marcali | 260/653 |
| 3,321,383 | 5/1967 | Scherer et al. | 260/653 |

FOREIGN PATENTS OR APPLICATIONS

| 1,600,040 | 8/1970 | France | 260/653 |

*Primary Examiner*—D. Horwitz
*Attorney, Agent, or Firm*—Burgess, Dinklage & Sprung

[57] ABSTRACT

A process for the purification of contaminated 1,1,1-trifluoro-2-chloro-2-bromoethane by reaction of the compound with organic amines, yielding 1,1,1-trifluoro-2-chloro-2-bromoethane of sufficient purity for use as an anaesthetic.

10 Claims, No Drawings

PROCESS FOR PURIFYING 1,1,1-TRIFLUORO-2-CHLORO-2-BROMOETHANE

This is a continuation of application Ser. No. 224,628 now abandoned, filed Feb. 8, 1972.

BACKGROUND OF THE INVENTION

This invention relates to a process for purifying 1,1,1-trifluoro-2-chloro-2-bromoethane.

1,1,1-trifluoro-2-chloro-2-bromoethane is known under the name "Halothan" as a valuable inhalation anaesthetic. Depending on the method of its manufacture it may contain small amounts of impurities, such as compounds of the type $CF_3 - CX = CY - CF_3$ in which X represents hydrogen, chlorine or bromine and Y represents chlorine or bromine. Such impurities can, however, not be tolerated in Halothan if it is to be used as an anaesthetic, and, therefore, they must be removed. Removal by distillation can be performed only with great difficulty. Consequently, a number of refining processes have been described in which contaminated Halothan is purified by treatment with anhydrous aluminum halides, as disclosed in German "Offenlegungsschrift" No. 1,543,089 or aqueous permanganate solution, as disclosed in German "Offenlegungsschrift" No. 1,543,101. In these processes, however, the great sensitivity of aluminum halides to moisture is disadvantageous, or, if potassium permanganate is used, the refining action is not as good.

It has now been found that 1,1,1-trifluoro-2-chloro-2-bromoethane which is contaminated mainly with compounds of the general formula $CF_3 - CX = CY - CF_3$ (X = hydrogen, chlorine or bromine, Y = chlorine or bromine) can be purified by putting it into intimate contact with one or more organic amines and recovering in a known manner the 1,1,1-trifluoro-2-chloro-2-bromoethane which has thus been freed of the impurities.

DESCRIPTION OF THE INVENTION

In general, the process of the present invention involves mixing the contamined 1,1,1-trifluoro-2-chloro-2-bromoethane with one or more different organic amines, allowing the mixture to react for a period of time at normal or elevated temperatures, and subsequently separating the pure 1,1,1-trifluoro-2-chloro-2-bromoethane. It is desirable to perform the separation by adding water to the reaction mixture whereby a phase separation occurs between the organic reaction mixture and the aqueous portion, separating the aqueous phase, and distilling the pure product out of the non-aqueous phase, after one or more additional purifications with water if desired. It is also possible, however, to fractionally distill the product of the reaction of the 1,1,1-trifluoro-2-chloro-2-bromoethane with the amines directly, the impurities and the unreacted amine remaining in the residue.

The amount of amine that is used can be varied within broad limits. It depends essentially only on the concentration of the impurities, at least 1 mole of amine being required per mole of impurity. It is desirable to operate with an appreciable excess of amine.

The more strongly basic amines, whose $pK_b$ value is less than 3 and which are solid or liquid under normal conditions, are particularly well suited for this purpose. These include the very basic acyclic and cyclic amino compounds, such as diethylene triamine and its higher homologs of the general formula $H_2N - (CH_2 - CH_2 - NH)_n - H$ wherein $n \geq 2$, such as triethylene tetramine (where $n = 3$), the aliphatic primary and secondary diamines with preferably 2 to 8 carbon atoms, ethanolamine, 1,3-propane diamine, piperidine, pyrrolidine etc., as well as mixtures thereof.

The purification according to the invention of contaminated 1,1,1-trifluoro-2-chloro-2-bromoethane by means of an amine is performed at a temperature between the solidification point and the boiling point of the mixture and, subsequent to reaction, the mixture is allowed to stand at room temperature or elevated temperature and settle. Generally, the higher the temperature of reaction, the shorter is the time required for the purification. The range between 20° and 50° C is especially suitable. The 1,1,1-trifluoro-2-chloro-2-bromoethane which is then separated in a known manner is free of the impurities present prior to the purification.

The following examples are illustrative of the process of the present invention. In order to learn how effective the process is, the concentrations of the impurities were in some cases deliberately increased. The analyses were performed by means of a gas chromatograph.

EXAMPLE 1

100 weight parts of 1,1,1-trifluoro-2-chloro-2-bromoethane containing a total of about 1200 ppm of impurities, mainly chlorine-substituted and/or bromine-substituted hexafluorobutene-2, was treated with 30 weight parts of piperidine and let stand for 3 hours at room temperature. Then the mixture was fractionally distilled at normal pressure, and 88 weight parts of 1,1,1-trifluoro-2-chloro-2-bromoethane of a boiling point of 49.7° C/742 Torr was obtained containing less than 1 ppm of impurities. The residue contained a crystalline mass and unreacted amine.

EXAMPLE 2

200 weight parts of 1,1,1-trifluoro-2-chloro-2-bromoethane containing a total of about 1500 ppm of impurities of the same kind as in Example 1 was mixed with 100 weight parts of diethylene triamine and let stand for 5 hours at room temperature. Then the mixture was distilled in a vacuum of 20 Torr, whereupon 170 weight parts of 1,1,1-trifluoro-2-chloro-2-bromoethane passes over at −26° C as the main fraction, having a total content of around 5 ppm of impurities.

EXAMPLE 3

A mixture of 150 weight parts of 1,1,1-trifluoro-2-chloro-2-bromoethane with a content of 560 ppm of 1,1,1,4,4,4-hexafluoro-2,3-dichlorobutene-2 and 40 weight parts of N,N-dimethyl-1,3-propanediamine was heated to 50° C and held at that temperature for half an hour such that the mixture barely boiled with a slight refluxing. After cooling, 150 parts by weight of water was added. Separation into a lower, organic phase and an upper, aqueous phase took place. The latter contained the impurities and the excess amine and was discarded. From the non-aqueous phase, after repeated washing with water and brief drying with anhydrous sodium sulfate, 135 weight parts of 1,1,1-trifluoro-2-chloro-2-bromoethane was obtained by distillation at normal pressure, and no 1,1,1,4,4,4-hexafluoro-2,3-dichlorobutene-2 could be detected in this product by gas chromatography.

EXAMPLE 4

300 weight parts of 1,1,1-trifluoro-2-chloro-2-bromoethane with about 2500 ppm of impurities similar to those of Example 1 was mixed with 80 weight parts of pyrrolidine and kept for one hour at such a temperature that the mixture barely boiled with slight refluxing. After cooling, 250 weight parts of water was added, whereupon separation into two phases took place. The lower, organic phase was distilled at normal pressure after two washings with water followed by brief drying with anhydrous sodium sulfate. At 49.8° C, 272 weight parts of 1,1,1-trifluoro-2-chloro-2-bromoethane passes over with an impurities content under 3 ppm.

EXAMPLE 5

A mixture of 300 weight parts of 1,1,1-trifluoro-2-chloro-2-bromoethane containing about 950 ppm of impurities, and 50 weight parts of ethanolamine, is let stand for 2 hours at 40° C. After the treatment that follows, which is analogous to Example 4, 265 weight parts of 1,1,1-trifluoro-2-chloro-2-bromoethane is obtained with less than 1 ppm of impurities.

It is to be understood that the Examples given are merely illustrative and that various modifications and applications may be made without departing from the spirit and scope of the invention as set forth in the appended claims.

What is claimed is:

1. A process for the purification of contaminated 1,1,1-trifluoro-2-chloro-2-bromoethane comprising:
   a. mixing 1,1,1-trifluoro-2-chloro-2-bromoethane containing impurities of compounds consisting essentially of the formula $CF_3-CX=CY-CF_3$ where X is hydrogen, chlorine or bromine and Y is chlorine or bromine, with at least one organic amine selected from the group consisting of acyclic amino compounds whose $pK_b$ is less than 3, cyclic amino compounds whose $pK_b$ value is less than 3, aliphatic primary diamines having 2 to 8 carbon atoms whose $pK_b$ value is less than 3 and aliphatic secondary diamines having 2 to 8 carbon atoms whose $pK_b$ value is less than 3 to form a reaction mixture consisting essentially of said 1,1,1-trifluoro-2-chloro-2-bromoethane, said impurities and said amine;
   b. reacting said impurity with said amine; and
   c. separating the purified 1,1,1-trifluoro-2-chloro-2-bromoethane from the resultant reaction mixture.

2. The process of claim 1 wherein the reaction is carried out at elevated temperatures.

3. The process of claim 1 wherein the reaction is carried out at a temperature of from about 20° C to 50° C.

4. The process of claim 1 wherein the separation of the purified product is carried out by
   a. adding water to the organic reaction mixture whereby aqueous and organic phases are formed;
   b. separating the aqueous phase from the organic phase; and
   c. distilling the purified product from the organic phase.

5. The process of claim 1 wherein the separation of the purified product is carried out by fractionally distilling the reaction mixture.

6. The process of claim 1 wherein the amine is of the general formula:

$H_2N - CH_2 - CH_2 - NH)_n - H$ where $n \geq 2$.

7. The process of claim 1 wherein at least one mole of amine per mole of impurity is present in the reaction mixture.

8. A process for the purification of contaminated 1,1,1-trifluoro-2-chloro-2-bromoethane comprising:
   a. mixing 1,1,1-trifluoro-2-chloro-2-bromoethane containing impurities consisting essentially of compounds of the formula $CF_3-CX=CY-CF_3$ where X is hydrogen, chlorine or bromine and Y is chlorine or bromine with at least one organic amine selected from the group consisting of diethylenetriamine, 1,3-propanediamine, piperidine, pyrrolidine, ethanolamine, ethylenediamine and N,N'-dimethyl-1,3-propanediamine and mixtures thereof to form a reaction mixture consisting essentially of 1,1,1-trifluoro-2-chloro-2-bromoethane, said impurities and said amine;
   b. reacting said impurity with said amine; and
   c. separating the purified 1,1,1-trifluoro-2-chloro-2-bromoethane from the resultant reaction mixture.

9. A process according to claim 8 wherein said amine is ethylene diamine.

10. A process according to claim 8 wherein said amine, is N,N-dimethyl-1,3-propane diamine.

* * * * *